United States Patent
Ebert et al.

(10) Patent No.: US 11,739,052 B2
(45) Date of Patent: Aug. 29, 2023

(54) PROCESS FOR THE PREPARATION OF ORGANOSULFATE SALTS OF AMINO ACIDS ESTERS

(71) Applicant: BASF SE, Ludwigshafen am Rhein (DE)

(72) Inventors: Sophia Ebert, Ludwigshafen am Rhein (DE); Dieter Boeckh, Ludwigshafen am Rhein (DE); Dawid Marczewski, Ludwigshafen am Rhein (DE); Stefano Scialla, Cincinnati, OH (US); Brian Joseph Loughnane, Cincinnati, OH (US); Frank Huelskoetter, Cincinnati, OH (US)

(73) Assignee: BASF SE, Ludwigshafen am Rhein (DE)

( * ) Notice: Subject to any disclaimer, the term of this patent is extended or adjusted under 35 U.S.C. 154(b) by 17 days.

(21) Appl. No.: 17/421,288

(22) PCT Filed: Dec. 18, 2019

(86) PCT No.: PCT/EP2019/085995
§ 371 (c)(1),
(2) Date: Jul. 7, 2021

(87) PCT Pub. No.: WO2020/144030
PCT Pub. Date: Jul. 16, 2020

(65) Prior Publication Data
US 2022/0144753 A1   May 12, 2022

(30) Foreign Application Priority Data
Jan. 8, 2019 (EP) .................................. 19150654

(51) Int. Cl.
*C07C 227/22* (2006.01)
*C07C 303/24* (2006.01)

(52) U.S. Cl.
CPC .......... *C07C 227/22* (2013.01); *C07C 303/24* (2013.01)

(58) Field of Classification Search
None
See application file for complete search history.

(56) References Cited

U.S. PATENT DOCUMENTS

| 4,550,137 A | 10/1985 | Dowbenko et al. |
| 2004/0053779 A1 | 3/2004 | Larrow et al. |
| 2014/0249320 A1 | 9/2014 | Hook et al. |
| 2018/0065984 A1 | 3/2018 | De et al. |
| 2021/0114971 A1* | 4/2021 | Venderbosch ........ C07C 227/22 |

FOREIGN PATENT DOCUMENTS

| AU | 2016236239 A1 | 8/2017 |
| CN | 1681590 A | 10/2005 |
| CN | 101631765 A | 1/2010 |
| EP | 0847987 A1 | 6/1998 |
| FR | 2977585 A1 | 1/2013 |
| JP | 49-076822 A | 7/1974 |
| JP | 51-036735 B2 | 10/1976 |
| JP | 10-168049 A | 6/1998 |
| SU | 1276661 A1 | 12/1986 |
| WO | 2011/002746 A1 | 1/2011 |
| WO | 2015/172158 A1 | 11/2015 |

OTHER PUBLICATIONS

Isobutanol ("Boiling Point", downloaded from https://pubchem.ncbi.nlm.nih.gov/compound/Isobutanol#section=Boiling-Point& fullscreen=true on Nov. 22, 2022) (Year: 2022).*
Lagasse ("sulfuric acid" (2018). In P. Lagasse, & Columbia University, The Columbia encyclopedia (8th ed.). Columbia University Press. Credo Reference: https://search.credoreference.com/content/entry/columency/sulfuric_acid/0?institutionId=743) (Year: 2018).*
Wikipedia ("Sulfuric Acid", captured on Dec. 7, 2017 by the Internet Archive: http://web.archive.org/web/20171207062825/https://en.wikipedia.org/wiki/Sulfuric_acid and downloaded on Nov. 30, 2022) (Year: 2017).*
European Search Report for EP Patent Application No. 19150654.2, dated Jul. 9, 2019, 03 pages.
Trivedi et al., "Task-Specific, Biodegradable Amino Acid Ionic Liquid Surfactants", ChemSusChem, vol. 4, Issue 5, Apr. 19, 2011, pp. 604-608.
International Search Report and Written Opinion received for PCT Patent Application No. PCT/EP2019/085995, dated Mar. 3, 2020, 6 pages.
Robin A. Cox, "Lactams in sulfuric acid. The mechanism of amide hydrolysis in weak to moderately strong aqueous mineral acid media", Canadian Journal of Chemistry, vol. 76, Issue 6, Jun. 1998, pp. 649-656.

* cited by examiner

*Primary Examiner* — Amy C Bonaparte
(74) *Attorney, Agent, or Firm* — Faegre Drinker Biddle & Reath LLP

(57) ABSTRACT

The present invention relates to a process for the synthesis of organosulfate salts of amino acid esters comprising the steps of reacting at least one lactam with at least 3 carbon atoms in the lactam ring with sulfuric acid in an aqueous solution followed by esterification of the reaction product of the previous step with at least 200 mol-% of at least one alcohol selected from the group consisting of linear alkyl alcohol containing one hydroxy group, branched alkyl alcohol containing one hydroxy group, linear alkylether alcohol containing one hydroxy group, branched alkylether alcohol containing one hydroxy group, phenoxyalkanols containing one hydroxy group, and mixtures thereof; followed optionally removal of water and/or removal of excess alcohol.

10 Claims, No Drawings

PROCESS FOR THE PREPARATION OF ORGANOSULFATE SALTS OF AMINO ACIDS ESTERS

CROSS-REFERENCE TO RELATED APPLICATIONS

This application is a national stage application (under 35 U.S.C. § 371) of PCT/EP2019/085995, filed Dec. 18, 2019, which claims benefit of European Application No. 19150654.2, filed Jan. 8, 2019, both of which are incorporated herein by reference in their entirety.

The invention relates to a process for the preparation of organosulfate salts of amino acids esters.

Organosulfate salts such as alkyl sulfate salts and alkylether sulfate salts are known to be water-soluble salts which are used as detergents or wettings agents.

Amino acid esters from amino acids with equal to or more than 3 carbon atoms can be synthesized from the corresponding lactams. This synthesis includes as a first step the ring-opening of the lactam to obtain the amino acid in presence of an acid, and as a second step the esterification reaction with an alcohol.

FR2977585B1 discloses a process for the synthesis of α-amino acid esters of $C_7$- to $C_{36}$-alcohols from the amino acid or its salt in presence of an acidic catalyst such as sulfuric acid in the presence of water, starting from amino acids or salts thereof.

WO2015172158 discloses salts of ethanesulfonic acid alpha and higher amino acids esters.

WO2011002746 discloses the preparation of amino acids esters with sulfuric acid

TRIVEDI, T. J. et al. ChemSusChem 2011, number 4, pages 604-608 describe a synthesis route to salts from alpha-$C_3$-$C_4$-amino acid esters and laurylsulfate which includes the formation of amino acid ester as hydrochloride salt, followed by ion exchange with sodium laurylsulfate.

SU1276661 discloses salts from protonated amino acid esters and anionic alkylsulfates. They are obtained from amino acids with 2 mol hexadecanol and excess sulfuric acid in dioxane.

JP49076822 and JP51036735 disclose a process for the preparation of amino acid ester salts with alkylsulfates by heating 1 mole of amino acid with at least 3 mole lauryl alcohol in presence of sulfuric acid. The synthesis is carried out in toluene as solvent.

Currently available methods for the synthesis of organosulfate salts of amino acids esters apply amino acids as starting materials, are carried out in organic solvents, and often involve an anion-exchange after the synthesis of the amino acid ester, replacing the anion as present in the esterification reaction with an organosulfate.

There is a continuous need for an improved process for the preparation of organosulfate salts of amino acids esters with high yield at fast reaction times, without handling of organic solvents and without handling of gaseous corrosive acids. There is also a need for a process for the preparation of organosulfates and amino acid esters in one reaction with high yield, reducing reaction time and complexity of the synthesis. There is also a need for a process which allows to react quantitatively amino acids and amino acid precursors such as lactams with alcohols with which have a low water solubility and can therefore only be dispersed in water to obtain organosulfate salts of amino acids esters.

There is a continuous need for amino acid ester salts which combine an amino acid ester active in detergent formulations with an organosulfate detergent for incorporation in improved detergent formulations for fabric and home care applications such as hard surface cleaning.

It was an object of the present invention to provide a process which complies with the above identified objectives and needs.

This goal was achieved by the present invention as described herein below and as reflected in the claims.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

Generally, as used herein, the term "obtainable by" means that corresponding products do not necessarily have to be produced (i.e. obtained) by the corresponding method or process described in the respective specific context, but also products are comprised which exhibit all features of a product produced (obtained) by said corresponding method or process, wherein said products were actually not produced (obtained) by such method or process. However, the term "obtainable by" also comprises the more limiting term "obtained by", i.e. products which were actually produced (obtained) by a method or process described in the respective specific context.

When used herein any definition requiring a compound or a substituent of a compound to consist of "at least a number of carbon atoms", number of carbon atoms refers to the total number of carbon atoms in said compound or substituent of a compound. For example for a substituent disclosed as "alkyl ether with at least 8 carbon atoms comprising alkylene oxide groups", the total number of at least 8 carbon atoms needs to be the sum of the number of carbon atoms of the alkyl moiety and the number of carbon atoms of the alkylene oxide moieties.

The term "containing one hydroxy group" means that only one group —OH is present. Any functionalized group derived from a hydroxy group such as an ether group is not considered to be an —OH group.

The present invention relates to a process for the synthesis of organosulfate salts of amino acid esters comprising the steps of
(i) reacting at least one lactam with at least 3 carbon atoms in the lactam ring with sulfuric acid in an aqueous solution;
(ii) esterification of the reaction product of step (i) with at least 200 mol-% of at least one alcohol selected from the group consisting of linear alkyl alcohol containing one hydroxy group, branched alkyl alcohol containing one hydroxy group, linear alkylether alcohol containing one hydroxy group, branched alkylether alcohol containing one hydroxy group, phenoxyalkanols containing one hydroxy group, and mixtures thereof;
(iii) optionally removal of water and/or removal of excess alcohol of step (ii).

Organosulfates are esters derived from alcohols and sulfuric acid. Organosulfates R—SO$_4$- comprise a SO$_4$ core and a R group which may be selected from the group consisting of linear alkyl, branched alkyl, linear alkylether, branched alkylether, and phenoxyalkyl.

Lactams are cyclic amides, starting with α-lactam (three ring atoms) followed by β-lactam (four ring atoms), γ-lactam (five ring atoms) and so on. When hydrolyzed, lactams form the corresponding α-, β-, γ-amino acid. All lactams with at least three carbon atoms in the lactam ring can be used in the process for the synthesis of organosulfate salts of amino acids. In one embodiment of the present invention, lactams with of from four to twelve carbon atoms in the lactam ring are used. In another embodiment of the present invention, lactams with of from five to seven carbon atoms in the lactam ring are used. In a further embodiment, a lactam with six carbon atoms in the lactam ring, ε-lactam, is used.

Reaction of the lactam ring takes place by reacting the at least one lactam with sulfuric acid. Reaction of the lactam ring with the sulfuric acid is carried out in an aqueous solution. In one embodiment of the present application the reaction of the lactam ring takes place by reacting the at least one lactam with sulfuric acid in an aqueous solution containing only water.

The term "free of water" means that the composition contains no more than 5 wt.-% of water based on the total amount of solvent, in another embodiment no more than 1 wt.-% of water based on the total amount of solvent, in a further embodiment the solvent contains no water at all.

The term "aqueous solution" means that the solvent contains more than 50 wt.-% of water based on the total amount of solvent. In a further embodiment the term means that the solvent contains more than 80 wt.-% of water based on the total amount of solvent. In another embodiment the term means that the solvent contains more than 95 wt.-% of water based on the total amount of solvent. In a further embodiment the term means that the solvent contains more than 99 wt.-% of water based on the total amount of solvent. In an even further embodiment the term means that the solvent contains only water.

In one embodiment of the present invention no additional solvent other than water is present in step (i) of the process.

In one embodiment of the present invention, the lactam is selected from the group consisting of a lactam with five carbon atoms in the lactam ring, and a lactam with six carbon atoms in the lactam ring, and the reaction with sulfuric acid is carried out in an aqueous solution. In another embodiment of the present invention, the lactam has five carbon atoms in the lactam ring and the reaction with sulfuric acid is carried out in an aqueous solution.

In one embodiment the lactam is either dissolved in water or is dispersed in an aqueous phase. Typical concentration of lactam in water is in the range of from 50% by weight to 99% by weight based on the total weight of lactam and water. In one embodiment of the present invention the concentration of lactam in water is in the range of from 55 to 90% by weight based on the total weight of the lactam and water. In a further embodiment the concentration of lactam in water is in the range of from 65 to 80% by weight based on the total weight of the lactam and water.

In one embodiment, sulfuric acid is used as concentrated sulfuric acid. In another embodiment, sulfuric acid is used as 96 to 98 wt.-% sulfuric acid solution in water. In a further embodiment sulfuric acid is used as 80 wt.-% sulfuric acid solution in water.

In one embodiment of the present invention the total amount of sulfuric acid is added at the beginning of the reaction to the at least one lactam. In another embodiment the sulfuric acid is added dropwise for a duration of from 0.1 to 10 h to the at least one lactam.

The molar ratio of sulfuric acid to lactam is in the range of from 90 to 200 mol-%. In one embodiment of the present invention the molar ratio of sulfuric acid to lactam is in the range of from 90 to 150 mol-%. In another embodiment the molar ratio of sulfuric acid to lactam is in the range of from 95 to 125 mol-%. In a further embodiment the molar ratio of sulfuric acid to lactam is 100 mol-%.

The reaction of the at least one lactam with sulfuric acid is carried out at temperatures of from 50 to 150° C. In one embodiment of the invention, the reaction is carried out at temperatures of from 80 to 140° C. In another embodiment the reaction is carried out at temperatures of from 90 to 130° C. In one embodiment of the present invention, the temperature is kept constant for the duration of the reaction. In another embodiment, the temperature is varied within the temperature range during the duration of the reaction. The reaction of the at least one lactam with sulfuric acid is carried out for a duration of from 0.1 to 15 hours. In another embodiment of the present invention the duration is of from 1 to 10 hours. In another embodiment the duration is of from 2 to 5 hours. In one embodiment of the present invention the reaction of the at least one lactam with sulfuric acid is carried out under atmospheric pressure. In another embodiment the reaction of the at least one lactam with sulfuric acid is carried out in a closed vessel under pressure of from 1 to 10 bar. In a further embodiment the reaction of the at least one lactam with sulfuric acid is carried out in a closed vessel under pressure of from 1 to 5 bar. In another embodiment the reaction of the at least one lactam with sulfuric acid is carried out in a closed vessel under pressure of from 1 to 4 bar. In one embodiment a protective atmosphere of for example nitrogen gas or argon gas is used to carry out the reaction. In another embodiment the reaction of the at least one lactam with sulfuric acid is carried at a temperature of from 50 to 150° C. at atmospheric pressure for a duration of 0.1 to 10 h. In a further embodiment of the present invention the reaction of the at least one lactam with sulfuric acid is carried at a temperature of from 90 to 130° C. for 3 hours under atmospheric pressure. In another embodiment of the present invention the reaction of the at least one lactam with sulfuric acid is carried at a temperature of from 50 to 150° C. for a duration of 0.1 to 10 h hours in a closed vessel under pressure of from 1.0 to 10 bar.

In step (ii) two parallel esterification reactions take place. One esterification reaction is the formation of an ester of the carboxylic group formed by ring-opening of the lactam with sulfuric acid and at least one alcohol selected from the group consisting of linear alkyl alcohol containing one hydroxy group, branched alkyl alcohol containing one hydroxy group, linear alkylether alcohol containing one hydroxy group, branched alkylether alcohol containing one hydroxy group, phenoxyalkanols containing one hydroxy group, and mixtures thereof. The other esterification reaction is the formation of an ester of sulfuric acid and at least one alcohol selected from the group consisting of linear alkyl alcohol containing one hydroxy group, branched alkyl alcohol containing one hydroxy group, linear alkylether alcohol containing one hydroxy group, branched alkylether alcohol containing one hydroxy group, and mixtures thereof.

In one embodiment of the present invention the reaction of the at least one lactam with sulfuric acid is carried out as a separate step (i) of the process. In another embodiment the reaction of the at least one lactam with sulfuric acid and at least one alcohol is carried out in one single step, i.e. step (i) is carried out in combination with step (ii), the esterification reaction with at least one alcohol selected from the group consisting of linear alkyl alcohol containing one hydroxy group, branched alkyl alcohol containing one hydroxy group, linear alkylether alcohol containing one hydroxy group, branched alkylether alcohol containing one hydroxy group, phenoxyalkanols containing one hydroxy group, and mixtures thereof. In a further embodiment the reaction of the at least one lactam with sulfuric acid in and the reaction with the at least one alcohol is carried out in one single step in an aqueous solution containing only water, i.e. step (i) is carried out in combination with step (ii), the esterification reaction with at least one alcohol selected from the group consisting of linear alkyl alcohol containing one hydroxy group, branched alkyl alcohol containing one hydroxy group, linear alkylether alcohol containing one hydroxy group, branched alkylether alcohol containing one hydroxy group, and mixtures thereof.

If step (ii) takes place as a separate step following step (i) of the process, the reaction of step (i) is carried out until the hydrolysis of the lactam ring is completed. Completed is to be understood in the sense of that no more hydrolysis can take place, either because all lactam rings are hydrolyzed or because no more hydrolysis is possible given the chemical nature of the reaction partners and their amounts.

The alcohol in step (ii) is added either as substance without additional solvent or dissolved in water. In one embodiment of the present invention, the at least one alcohol is selected from the group consisting of linear alkyl alcohol containing one hydroxy group, branched alkyl alcohol containing one hydroxy group, linear alkylether alcohol containing one hydroxy group, branched alkylether alcohol containing one hydroxy group, phenoxyalkanols containing one hydroxy group, and mixtures thereof.

In one embodiment of the present invention, at least one linear or branched $C_2$- to $C_{36}$-alcohol containing one hydroxy group is used. In another embodiment at least one $C_8$- to $C_{22}$-fatty alcohol containing one hydroxy group is used. In another embodiment a mixture of $C_{16}$- and $C_{18}$-fatty alcohols each containing one hydroxy group is used. In another embodiment a mixture of $C_{18}$- and $C_{22}$-fatty alcohols each containing one hydroxy group is used. In one embodiment at least one branched $C_9$- to $C_{17}$ alcohol is used. In a further embodiment linear or branched $C_8$- to $C_{10}$-mono-alcohols containing one hydroxy group are used. In a further embodiment 2-propylheptanol or 2-ethylhexanol are used. In an even further embodiment 2-ethylhexanol is used.

In another embodiment, alkylether alcohols are used. Alkylether alcohols are for example alkyl alcohols alkoxylated with ethylene oxide, and/or propylene oxide, and/or butylene oxide. In one embodiment of the present invention, at least one linear or branched $C_2$- to $C_{36}$-alcohol containing one hydroxy group alkoxylated with ethylene oxide, and/or propylene oxide, and/or butylene oxide is used. In another embodiment at least one $C_8$- to $C_{22}$-alcohol containing one hydroxy group alkoxylated with ethylene oxide, and/or propylene oxide, and/or butylene oxide is used. Alkoxylation of the alcohol is either carried out with only one alkylene oxide or with more than one alkylene oxide. If more than one alkylene oxide is used, the resulting alkylether alcohols comprises either randomly distributed alkylene oxide units or a block of one alkylene oxide followed by a block of another alkylene oxide. In one embodiment of the present invention, alkyl alcohols alkoxylated with only a single alkylene oxide are used. In a further embodiment, alkyl alcohols alkoxylated with a first alkylene oxide followed by alkoxylation with a second alkylene oxide, thereby forming a block structure of different alkylene oxide blocks, are used. In even another embodiment, alkoxylated 2-propylheptanole is used.

In a further embodiment of the present invention, at least one phenoxyalkanol is used. In another embodiment phenoxyethanol is used.

In one embodiment of the present invention the molar ratio of alcohol containing one hydroxy group to lactam with at least 3 carbon atoms is in the range of from 200 to 400 mol-%. In another embodiment the molar ratio of alcohol containing one hydroxy group to lactam with at least 3 carbon atoms is in the range of from 200 to 300 mol-%. In another embodiment the molar ratio of alcohol containing one hydroxy group to lactam with at least 3 carbon atoms is in the range of from 200 to 250 mol-%.

In another embodiment of the present invention the molar ratio of alcohol containing one hydroxy group to sulfuric acid is in the range of from 200 mol-% to 400 mol-%. In a further embodiment the molar ratio of alcohol containing one hydroxy group to sulfuric acid is in the range of from 200 mol-% to 300 mol-%. In another embodiment the molar ratio of alcohol containing one hydroxy group to sulfuric acid is in the range of from 200 mol-% to 250 mol-%.

The esterification reaction of step (ii) is carried out at temperatures in the range of from 80 to 200° C. In another embodiment of the present invention the esterification reaction is carried out at temperatures in the range of from 120 to 140° C. In one embodiment of the present invention, the temperature is kept constant for the duration of the reaction. In another embodiment, the temperature is varied within the temperature range during the duration of the reaction. The duration of the esterification reaction of step (ii) is from 1 to 30 h. In another embodiment of the present invention, the duration of the esterification reaction is from 2 to 5 h. In a further embodiment the esterification is carried out in a closed vessel under pressure of from 1 to 10 bar. In a further embodiment the esterification is carried out in a closed vessel under pressure of from 1 to 5 bar. In another embodiment the esterification is carried out in a closed vessel under pressure of from 1 to 4 bar. In one embodiment a protective atmosphere of for example nitrogen gas or argon gas is used to carry out the reaction. In another embodiment the esterification is carried at a temperature of from 80 to 200° C. at atmospheric pressure for a duration of 0.1 to 10 h. In a further embodiment of the present invention the esterification is carried at a temperature of from 90 to 130° C. for 3 hours under atmospheric pressure. In another embodiment of the present invention the reaction of the esterification is carried at a temperature of from 80 to 200° C. for a duration of 0.1 to 30 h hours in a closed vessel under pressure of from 1.0 to 10 bar.

In one embodiment of the present invention combined steps (i) and (ii) are carried out by mixing at least one lactam with at least 3 carbon atoms in an aqueous solution and at least one alcohol selected from the group consisting of linear alkyl alcohol containing one hydroxy group, branched alkyl alcohol containing one hydroxy group, linear alkylether alcohol containing one hydroxy group, branched alkylether alcohol containing one hydroxy group, phenoxyalkanols containing one hydroxy group, and mixtures thereof, addition of sulfuric acid followed by sealing of the vessel to react the mixture at a temperature of 80 to 200° C. for 1 to 30 h. In a further embodiment of the present invention combined steps (i) and (ii) are carried out by mixing at least one lactam with at least 3 carbon atoms and at least one alcohol selected from the group consisting of linear alkyl alcohol containing one hydroxy group, branched alkyl alcohol containing one hydroxy group, linear alkylether alcohol containing one hydroxy group, branched alkylether alcohol containing one hydroxy group, phenoxyalkanols containing one hydroxy group, and mixtures thereof, addition of sulfuric acid followed by sealing of the vessel to react the mixture at a temperature of 80 to 200° C. for 1 to 30 h at a pressure of from 1.0 to 10 bar.

Following step (ii) or following the combined steps (i) and (ii) water and/or excess alcohol can be removed. Removal of water and alcohol can be carried out by all techniques known in the art, for example by application of a vacuum. In one embodiment of the present invention step (iii), the optional removal of water and/or excess of alcohol, is carried out applying a vacuum in the range of from 0.1 mbar to 800 mbar. In another embodiment vacuum in the range of from 1 mbar to 500 mbar is applied. In a further embodiment vacuum in the range of from 10 mbar to 100 mbar is applied

EXAMPLES

Methods

1H NMR measured in MeOD with Bruker Avance 400 MHz spectrometer.

Hydroxy values are determined according to DIN 53240-1 as of 2016.

Example 1: 6-amino-hexane acid-diethylene glycol-C12/C14-alkylester as diethylene glycol-C12/C14-alkylsulfuric acid salt In a 4-neck vessel with thermometer, reflux condenser, nitrogen inlet, dropping funnel, and stirrer, 28.3 g caprolactam (80 wt.-% aqueous solution) and 11.5 g water are placed, and 20.8 g concentrated sulfuric acid are added within 5 minutes. The temperature raises from room temperature to 60° C. during the addition. The mixture is heated to reflux and stirred for 4 hours. 130.7 g C12/C14 fatty alcohol, ethoxylated with 2 mole ethylene oxide (hydroxy value 185 mgKOH/g) are placed and heated to 115° C. Water is allowed to distill off from the reaction mixture. The reaction mixture is stirred for 4 hours under these conditions. 155.0 g of an off-white soft wax is obtained. 1H-NMR in MeOD indicates complete conversion to 6-amino-hexane acid-diethylene glycol-C12/C14-alkylester as diethylene glycol-C12/C14-alkylsulfuric acid salt.

Example 2: 6-amino-hexane acid-2-ethyl-hexylester as 2-ethyl-hexylsulfuric acid salt In a 4-neck vessel with thermometer, reflux condenser, nitrogen inlet, dropping funnel, and stirrer, 99.0 g caprolactam (80 wt.-% aqueous solution), 40.3 g water and 227.9 g 2-ethylhexanol are placed. 72.9 g concentrated sulfuric acid are added within 15 minutes. The temperature raises from room temperature to 50° C. during the addition. The mixture is heated to reflux and stirred for 3 hours under reflux. The reflux condenser is replaced by a distillation head and water is allowed to distill off from the reaction mixture at 107-130° C. The reaction mixture is stirred for 4 hours under these conditions. 310.0 g of a light yellow oil is obtained. 1H-NMR in MeOD indicates 92% conversion to 6-amino-hexane acid-2-ethyl-hexylester as ethyl-hexylsulfuric acid salt.

Example 3: 6-amino-hexane acid-2-ethyl-hexylester as 2-ethyl-hexylsulfuric acid salt (Under Pressure)

In a 50 ml round bottom glass pressure vessel, stable up to 10 bar, with magnetic stirrer, 6.3 g caprolactam (90 wt.-% aqueous solution), and 16.3 g 2-ethylhexanol are placed. 5.2 g concentrated sulfuric acid are added within 15 minutes. The temperature raises from room temperature to 50° C. during the addition. The vessel is closed and placed in an oil bath. The oil bath is heated to 135° C., and the mixture is stirred for 3 hours under these conditions in the closed vessel. The mixture is transferred to a 3-neck vessel with stirrer, thermometer, and nitrogen inlet. Under a constant stream of nitrogen through the liquid, the reaction mixture is stirred for 6.5 hours at 135° C. oil bath temperature. 21.0 g of a yellow oil is obtained. 1H-NMR in MeOD indicates 98% conversion to 6-amino-hexane acid-2-ethyl-hexylester as ethyl-hexylsulfuric acid salt.

The invention claimed is:

1. A process for the synthesis of organosulfate salts of amino acid esters comprising the steps of
    (i) reacting at least one lactam with at least 3 carbon atoms in the lactam ring with sulfuric acid in an aqueous solution, wherein the concentration of lactam in water is in the range of from 50% to 90% by weight based on the total weight of lactam and water;
    (ii) esterifying the reaction product of step (i) with at least 200 mol-% of at least one alcohol selected from the group consisting of a linear alkyl alcohol containing one hydroxy group, a branched alkyl alcohol containing one hydroxy group, a linear alkylether alcohol containing one hydroxy group, a branched alkylether alcohol containing one hydroxy group, phenoxyalkanols containing one hydroxy group, and mixtures thereof; and
    (iii) optionally removing water and/or removing excess alcohol of step (ii).

2. The process according to claim 1, wherein step (i) and (ii) are carried out in one single step.

3. The process according to claim 1, wherein the molar ratio of sulfuric acid to lactam is in the range of from 90 to 200 mol-% based on 100 mol % of the lactam.

4. The process according to claim 1, wherein the molar ratio of alcohol containing one hydroxy group to lactam with at least 3 carbon atoms is in the range of from 200 mol-% to 400 mol-% based on 100 mol % of the lactam.

5. The process according to claim 1, wherein the molar ratio of alcohol containing one hydroxy group to sulfuric acid is in the range of from 200 mol-% to 400 mol-% based on 100 mol % of the sulfuric acid.

6. The process according to claim 2, wherein the combined step (i) and (ii) comprises reacting a mixture of sulfuric acid, at least one lactam and at least one alcohol at a temperature of 80 to 200° C. for 1 to 30 h.

7. The process according to claim 2, wherein the combined step (i) and (ii) comprises reacting a mixture of sulfuric acid, at least one lactam and at least one alcohol in a closed vessel under pressure of from 1.0 up to 10.0 bar.

8. The process according to claim 1, wherein the lactam used in step (i) is a ε-lactam.

9. The process according to claim 1 wherein the concentration of lactam in water is in the range of from 55% to 90% by weight based on the total weight of lactam and water.

10. The process according to claim 1 wherein the concentration of lactam in water is in the range of from 55% to 80% by weight based on the total weight of lactam and water.

* * * * *